US00PP35765P2

(12) United States Plant Patent
Mitchell

(10) Patent No.: US PP35,765 P2
(45) Date of Patent: Apr. 23, 2024

(54) ***FORSYTHIA* PLANT NAMED 'DISCOVERY'**

(50) Latin Name: ***Forsythia* x *intermedia***
Varietal Denomination: Discovery

(71) Applicant: Elizabeth Mitchell, Oxford (GB)

(72) Inventor: Elizabeth Mitchell, Oxford (GB)

( * ) Notice: Subject to any disclaimer, the term of this patent is extended or adjusted under 35 U.S.C. 154(b) by 0 days.

(21) Appl. No.: 18/185,701

(22) Filed: Mar. 17, 2023

(51) Int. Cl.
*A01H 5/00* (2018.01)
*A01H 6/00* (2018.01)

(52) U.S. Cl.
USPC ..... Plt./230

(58) Field of Classification Search
USPC ..... Plt./230
See application file for complete search history.

(56) References Cited

PUBLICATIONS https://www.rhs.org.uk/plants/plants-blogs/plants/march-2022/forsythia-x-intermedia-discovery (3 pages total).*

* cited by examiner

*Primary Examiner* — Susan McCormick Ewoldt
(74) *Attorney, Agent, or Firm* — Weatherly IP Solutions, LLC; James M. Weatherly

(57) ABSTRACT

A new cultivar of *Forsythia* plant named 'Discovery' that is characterized by its upright plant habit with arching branches and variegated foliage in which the young leaves exhibit green centers and broad bright yellow marginal bands. The golden yellow flowers of 'Discovery' emerge early in spring, before the development of the new season's foliage and at peak flowering completely cover the plant.

3 Drawing Sheets

Genus and species: *Forsythia* x *intermedia*.
Variety denomination: 'Discovery'.

BACKGROUND

The present disclosure relates to a new and distinct cultivar of *Forsythia* plant, a shrub that is grown for use as an ornamental landscape and container plant. The new variety is known botanically as *Forsythia* x *intermedia* and will be referred to hereinafter by the cultivar name 'Discovery'

'Discovery' was first observed by the inventor in 2007 as a naturally occurring branch sport which was growing on an unnamed single plant of *Forsythia* x *intermedia* (variety unknown) in the inventor's garden in Oxford, United Kingdom. The unnamed sport parent variety bears entirely green foliage, whereas 'Discovery" bears variegated leaves consisting of green centers and yellow marginal bands. Upon discovery of the variegated branch, the inventor rooted a small number of softwood cuttings in order to establish the variegated form on its own roots, to evaluate its stability, and to increase numbers for commercial introduction.

The inventor has determined from repeated cycles of asexual reproduction that 'Discovery' is a stable cultivar which reproduces and remains true-to-type.

SUMMARY

The following traits have been repeatedly observed and represent the distinguishing characteristics of 'Discovery'. 'Discovery' has not been tested under all possible conditions and phenotypic differences may be observed with variations in environmental, climatic, and cultural conditions, without however, any variance in genotype.

1. 'Discovery' is moderately vigorous and exhibits an upright plant habit with arching branches
2. The leaves of 'Discovery' are variegated, with green centers and yellow or cream-yellow marginal bands.
3. The margins of new foliage growth of 'Discovery' are broad and bright yellow in color.
4. The margins of the mature foliage of 'Discovery' are narrow and cream-yellow in color.
5. The flowers of 'Discovery' emerge early in spring, before the development of the new season's foliage.
6. The flowers of 'Discovery' are bright golden yellow in color and at peak flowering completely cover the plant.

DESCRIPTION OF THE PHOTOGRAPHS

The accompanying color photographs illustrate the overall appearance of the new *Forsythia* cultivar 'Discovery' showing the colors as true as it is reasonably possible to obtain in colored reproductions of this type. Colors in the photographs may differ from the color values cited in the detailed botanical description, which accurately describes the observed colors of 'Discovery'.

DESCRIPTION OF THE NEW VARIETY

Figure 1:
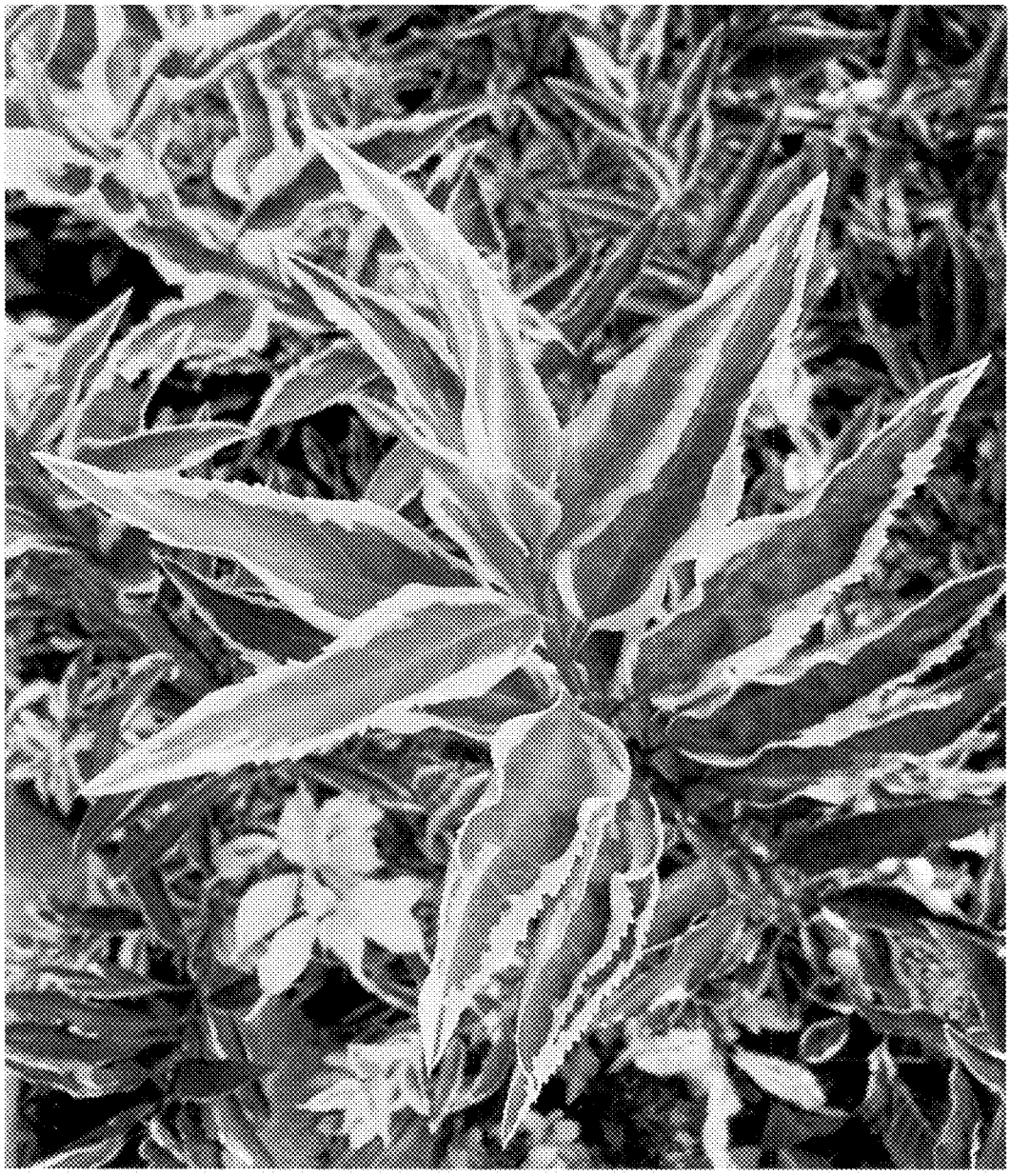
FIG. 1 depicts the early spring, new foliage growth of 'Discovery' showing the broad bright yellow leaf margins of the young foliage and the narrow cream-yellow margins of the older, mature foliage. The illustrated plant has been grown in a 2-gallon container outside in Santa Barbara, California.
Figure 2:
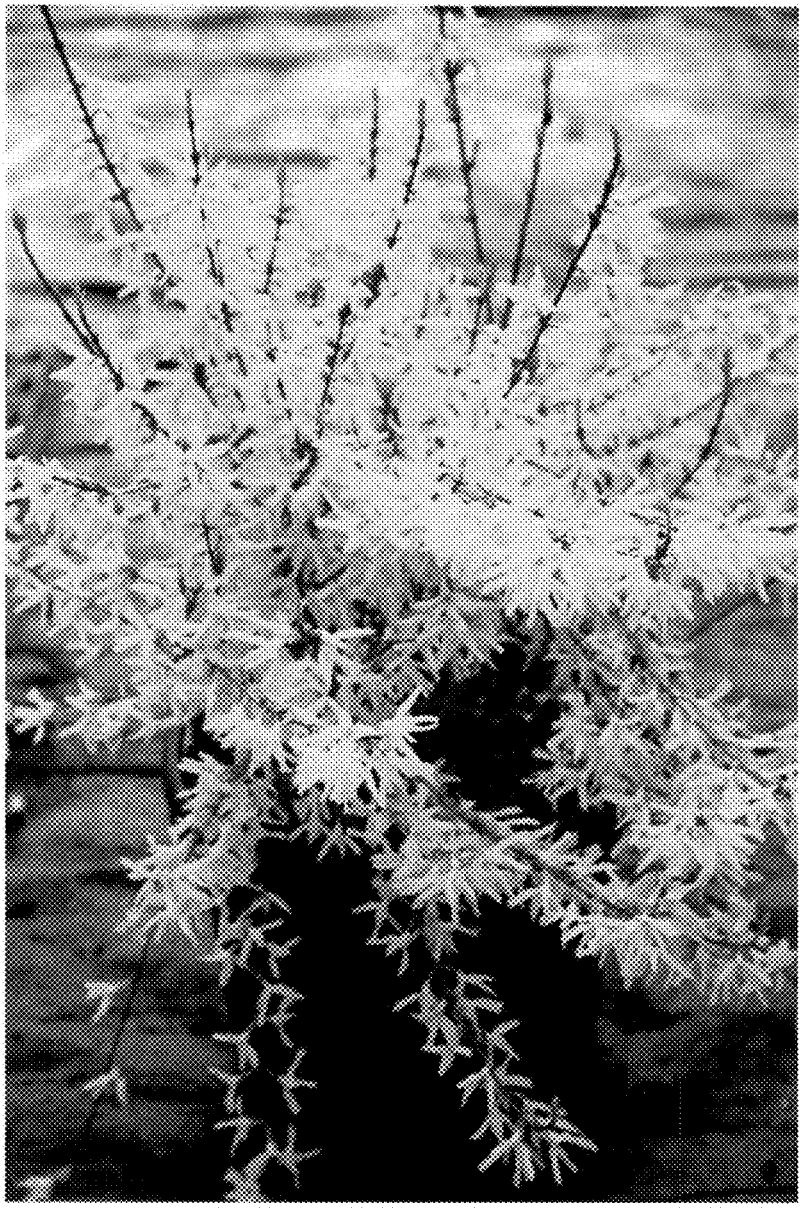
FIG. 2 depicts a plant of 'Discovery' in full flower in April. The illustrated plant has been grown in a 2-gallon container outside in Santa Barbara, California.
Figure 3:
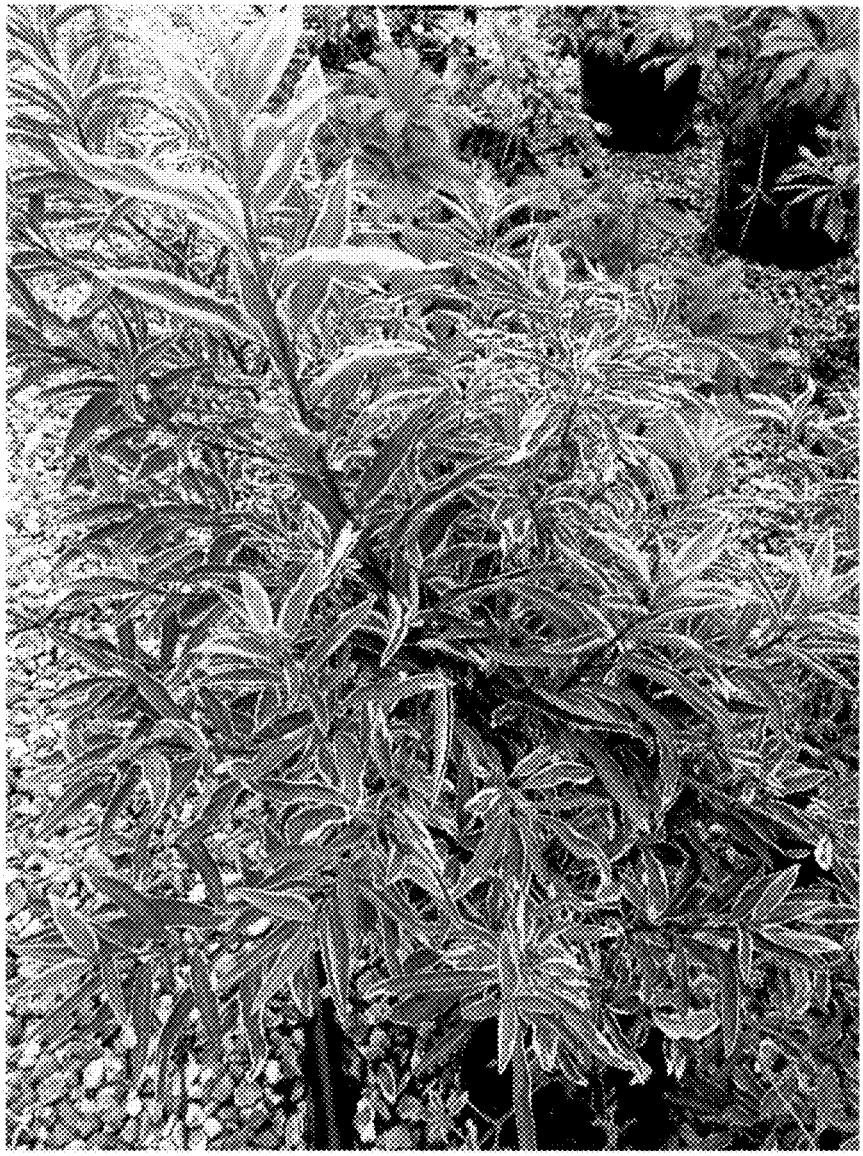
FIG. 3 depicts a plant of 'Discovery' in late summer when flowering has finished. The illustrated plant has been grown in a 3-gallon container outside in Romsey, Hampshire, United Kingdom.

The following is a detailed description of the new *Forsythia* cultivar named 'Discovery'. Data was collected in Santa Barbara, California from a plant grown out-of-doors in a 2-gallon container. Phenotypic differences may be observed with variations in environmental, climatic, and cultural conditions, without however, any difference in genotype. Color determinations are in accordance with the 2007 edition of The Royal Horticultural Society Colour Chart except where general color terms of ordinary dictionary significance are used.

Classification:

*Family*.—Oleaceae.

*Genus*.—*Forsythia*.

*Species*.—x *intermedia*.

*Denomination*.—'Discovery'.

*Common name*.—*Forsythia*.

Plant:

*Plant type*.—Shrub.

*Plant use*.—For container and landscape.

*Plant parentage*.—*Forsythia* x *intermedia* 'Discovery' occurred as a naturally occurring branch mutation found growing on a single plant of an unnamed non-variegated variety of *Forsythia* x *intermedia*.

*Plant vigor*.—Moderate, less vigorous than non-variegated varieties of *Forsythia*.

*Plant shape*.—Upright with arching stems, rounded profile overall.

*Branching habit*.—Open.

*Dimensions after* 1 *year*.—75 cm in height and 75 cm. in width.

*Dimensions after* 2 *years*.—3 m in height, 3 m in width.

*Plant hardiness*.—USDA Zone 5.

*Bloom season*.—Flowers are borne from early spring until early summer.

Propagation, growing:

*Asexual propagation method*.—Semi-ripe softwood cuttings taken from mid-May onwards.

*Rooting time*.—3-4 weeks to produce a well-rooted young plant suitable for transplanting.

*Roots*.—Fibrous, densely branching, color NN155D.

*Growing conditions*.—Grow and plant in full sun or partial shade, in well-draining soils or proprietary growing medium.

*Crop time*.—12-14 months to fill out a 1-gallon or 2-gallon container. Additional growing seasons are required to fill out larger containers.

*Pest and disease resistance or susceptibility*.—None specific to the variety.

Stem, branches:

*Description*.—A short and thick stem is formed below the first node at which the plant has been pinched or stopped to encourage production of basal branches.

*Stem*.—Shape: Terete. Dimensions: 2 cm-4 cm in length, 1 cm in diameter. Surface: Lignified, bark paper-like and peeling. Bark color: Ranges between 197D and 199C.

*Branches*.—Shape: Terete. Dimensions: Up to 70 cm in length, 6 mm in diameter towards base, 3 mm in diameter towards apex, Surface: Smooth, glabrous. Color: 144C towards base, becoming red-brown 178A towards apex.

*Internode distance*.—0.5 cm-2 cm.

Foliage:

*Foliage type*.—Deciduous.

*Leaf attachment*.—Petiolate.

*Leaf arrangement*.—Opposite.

*Leaf division*.—Simple.

*Leaf shape*.—Lanceolate.

*Leaf texture*.—Smooth, glabrous.

*Leaf appearance* (*adaxial surface*).—Semi-glossy.

*Leaf appearance* (*abaxial surface*).—Matte.

*Leaf length*.—9 cm.

*Leaf width*.—3.3 cm.

*Leaf variegation, description*.—Young leaves contain a green central section which lies within broad cream or cream-yellow marginal bands. The marginal bands extend around the entire perimeter of the leaf, including the apex, and for a distance between 2 mm and 4 mm inward from the leaf edge. The margin bands are replaced by expanding green centers as the leaf ages, until only a fine cream-colored margin remains.

*Leaf color, variegation*.—New growth, younger shoots, adaxial surface: Central section: 138A. Marginal band: 9A, 2 mm-4 mm in width. New growth, younger shoots, abaxial surface: Central section: N138A. Marginal band: 8B, 2 mm-4 mm in width. Older growth, adaxial surface: Central section: 137B. Marginal band: 9C, 1 mm in width or less (the margin edge itself). Older growth, abaxial surface: Central section: N138A. Marginal band: 8B, 1 mm in width or less (the margin edge itself).

*Leaf apex*.—Acute.

*Leaf base*.—Obtuse.

*Leaf margin* (*new growth, younger shoots*).—Serrated, 10-18 teeth concentrated in the mid-length of each leaf margin and generally absent towards base and apex. Tooth depth 1 mm-2 mm.

*Leaf margin* (*older growth*).—Mostly entire, occasional slight depressions and undulating.

*Venation* (*both surfaces*).—Pinnate, color 142C.

Petioles:

*Shape*.—Sulcate.

*Dimensions*.—10 mm-14 mm in length, 1.5 mm in width and depth.

*Color*.—183D.

*Surfaces*.—Glabrous.

Inflorescence:

*Inflorescence type, shape*.—Single, star-shaped flowers.

*Inflorescence arrangement*.—Solitary or in pairs at each node.

*Inflorescence dimensions* (*flowers fully open, petals reflexed*).—3.0 cm in diameter, 2.5 cm in height.

*Inflorescence quantity*.—Very numerous, approximately 500-600 (observed plant).

*Flower attachment* (*buds, flowers*).—Very short pedicels or sessile.

*Pedicels* (*where present*).—Up to 2 mm in length, 0.75 mm in diameter, puberulent, color 182C.

*Flowering time*.—Early spring to early summer.

*Flower shape*.—Salverform.

*Flower fragrance*.—None observed.

*Lastingness of flowers*.—Up to 7 days in spring, and 5 days in summer.

*Persistence of flowers*.—Self-cleaning.

Buds:

*Bud color* (*prior to petal emergence*).—Ranges between 165A and 165B.

*Bud color* (*emerging tightly-folded petals*).—2B.

*Bud shape*.—Ovoid.

*Bud dimensions*.—Up to 6 mm in length, 2.5 mm in diameter.

*Bud surface*.—Puberulent.

*Bud apex*.—Rounded.

*Bud base*.—Obtuse.

Calyx:

*Calyx shape*.—Funnelform, consisting of four sepals fused at base.

*Calyx diameter*.—12 mm across opposite sepal apices.

Sepals:

*Sepal quantity, arrangement*.—4 in number, fused at base then free, rotate.

*Sepal surface* (*both surfaces*).—Glabrous.

*Sepal shape*.—Oblanceolate.

*Sepal color* (*both surfaces*).—144B.

*Sepal dimensions*.—3 mm-4 mm in length, 2 mm in width.

*Sepal apex*.—Rounded.

*Sepal base*.—Truncate.

*Sepal margins*.—Smooth, entire.

Corolla:

*Corolla shape*.—Short tubular.

*Corolla color* (*both surfaces*).—8A.

*Corolla dimensions*.—3 mm. in length and 1 mm in diameter.

*Corolla surface* (*both surfaces*).—Glabrous.

Petals:

*Petal quantity, arrangement*.—4 in number, fused at base then free, rotate.

*Petal surface* (*both surfaces*).—Glabrous.

*Petal shape*.—Oblanceolate.

*Petal color* (*both surfaces*).—9B.

*Petal dimensions*.—9 mm-12 mm in length, 3 mm in width.

*Petal apex*.—Rounded.

*Petal base*.—Truncate.

*Petal margins*.—Smooth, entire.

Reproductive organs:

*Stamens*.—2.

*Filaments*.—Attachment: Adnate to interior of corolla tube. Dimensions: 5 mm in length, less than 0.5 mm in diameter. Color: 8A.

*Anthers*.—Ovoid, 1.5 mm in length, 1.0 mm in diameter.

*Anther color*.—8A.

*Pollen*.—Abundant, color 8A.

*Pistil*.—1.

*Stigma shape, dimensions*.—Orbicular, 1.0 mm-1.5 mm in diameter.

*Stigma surface*.—Glabrous.

*Stigma color*.—8A.

*Ovary*.—Superior, globose, 1.5 mm in diameter, color 145A.

Fruit and seed: None observed.

COMPARISON WITH PARENT VARIETY

'Discovery' is distinguished from its sport parent, a variety of *Forsythia* x *intermedia*, by the variegation of its foliage. Whereas 'Discovery' bears variegated leaves with green centers and yellow margins, the leaves of *Forsythia* x *intermedia* are entirely green in color.

COMPARISON WITH KNOWN VARIETIES

In general, varieties of *Forsythia* x *intermedia* are non-variegated. The variety *Forsythia* x *intermedia* 'McKCitrine' (U.S. Plant Pat. No. 16,464) is variegated and may be compared with 'Discovery' by the colors of the variegated leaves. Whereas the leaves of 'Discovery' exhibit green centers and yellow marginal bands, the leaves of 'McKCitrine' first open entirely yellow in color and then develop leaves with yellow-green margins and darker yellow-green centers.

I claim:

1. A new and distinct cultivar of *Forsythia* Plant Named 'Discovery' as described and illustrated herein.

* * * * *